United States Patent [19]

Hasegawa

[11] Patent Number: 5,800,355

[45] Date of Patent: Sep. 1, 1998

[54] IMAGE PROCESSING APPARATUS AND METHOD FOR QUANTITATIVELY DETECTING AND CORRECTING THE TWIST BETWEEN IMAGES

[75] Inventor: Hyoji Hasegawa, Tochigi-ken, Japan

[73] Assignee: Kabushiki Kaisha Toshiba, Kawasaki, Japan

[21] Appl. No.: 719,548

[22] Filed: Sep. 25, 1996

[30] Foreign Application Priority Data

Sep. 27, 1995 [JP] Japan .................... 7-248204

[51] Int. Cl.$^6$ ............................ A61B 6/00
[52] U.S. Cl. ............................ 600/436; 382/128
[58] Field of Search .................. 128/659, 654, 128/653.1, 653.2; 378/62, 98.5; 382/128, 289, 296, 131; 250/363.04, 363.05, 363.07, 363.09; 600/407, 410, 420, 436

[56] References Cited

U.S. PATENT DOCUMENTS

| | | | |
|---|---|---|---|
| 4,033,335 | 7/1977 | Nickles | 128/2.05 R |
| 4,245,647 | 1/1981 | Randall | 128/659 |
| 4,547,892 | 10/1985 | Richey et al. | 378/8 |
| 4,585,008 | 4/1986 | Jarkewicz | 128/654 |
| 4,922,543 | 5/1990 | Ahlbom et al. | 382/48 |
| 5,027,227 | 6/1991 | Kita | 358/488 |
| 5,063,605 | 11/1991 | Samad | 382/44 |
| 5,065,435 | 11/1991 | Oe | 382/6 |
| 5,099,846 | 3/1992 | Hardy | 128/653.1 |
| 5,164,997 | 11/1992 | Kumagai | 382/46 |
| 5,286,718 | 2/1994 | Elliott | 514/54 |
| 5,381,791 | 1/1995 | Quan | 128/659 |
| 5,398,684 | 3/1995 | Hardy | 128/653.1 |
| 5,421,331 | 6/1995 | Devito et al. | 128/659 |
| 5,423,316 | 6/1995 | Hawman et al. | 128/653.1 |
| 5,429,135 | 7/1995 | Hawman et al. | 128/659 |
| 5,431,161 | 7/1995 | Ryals et al. | 128/653.1 |
| 5,447,154 | 9/1995 | Cinquin et al. | 128/653.1 |
| 5,570,430 | 10/1996 | Sheehan et al. | 382/128 |
| 5,623,560 | 4/1997 | Nakajima et al. | 382/295 |

OTHER PUBLICATIONS

S. Kumita et al. "Assessment of Left Ventricular Function With $^{99m}$Tc–MIBI Gated Myocardial SPECT Using 3 Head Rotating Gamma Cammera" Jpn J Nucl Med 1994;31: 43–52.

*Primary Examiner*—Marvin M. Lateef
*Assistant Examiner*—Eleni Mantis Mercader
*Attorney, Agent, or Firm*—Oblon, Spivak, McClelland, Maier & Neustadt, P.C.

[57] ABSTRACT

Radiotracer is dosed to an object to detect radiation rays emitted from the radiotracer. The detection is performed with R waves of an electrocardiogram serving as a trigger at the end of diastole of the myocardium and the end of systole of the same during a predetermined number of heart beats. Detected radiation-ray data is used to reconstruct a SPECT short axis image (an ED image) at the end of the diastole and a SPECT short axis image (an ES image) at the end of systole, each of which is formed of several slices. All slices of the SPECT short axis image are developed on a polar coordinate to make functional maps (bull's-eye map). The amount of shift of the pattern of the segment value of the functional map of the ED image and the segment value of the functional map of the ES image is obtained for each slice by calculating the sum of products. The segment value for each slice is rotated on the functional map by the obtained amount so that the influence of the twist is corrected.

18 Claims, 6 Drawing Sheets

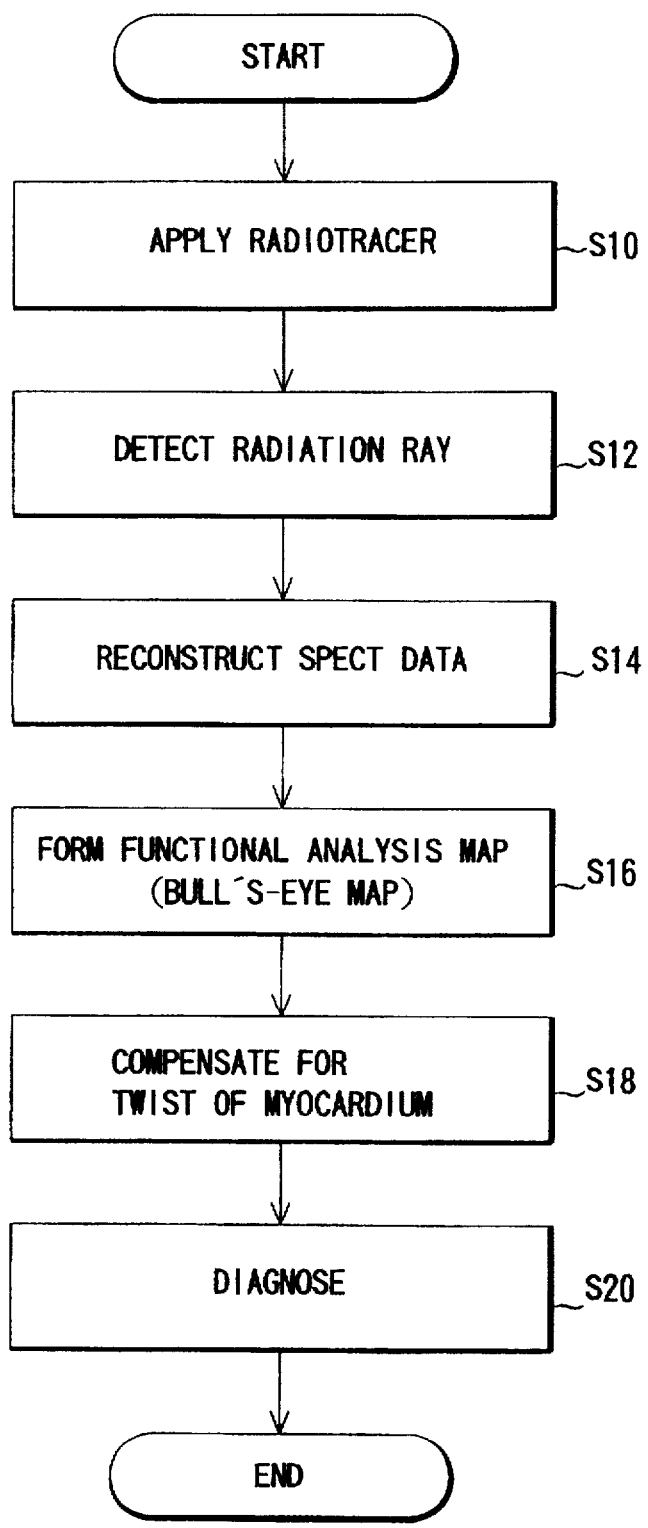
F I G. 3

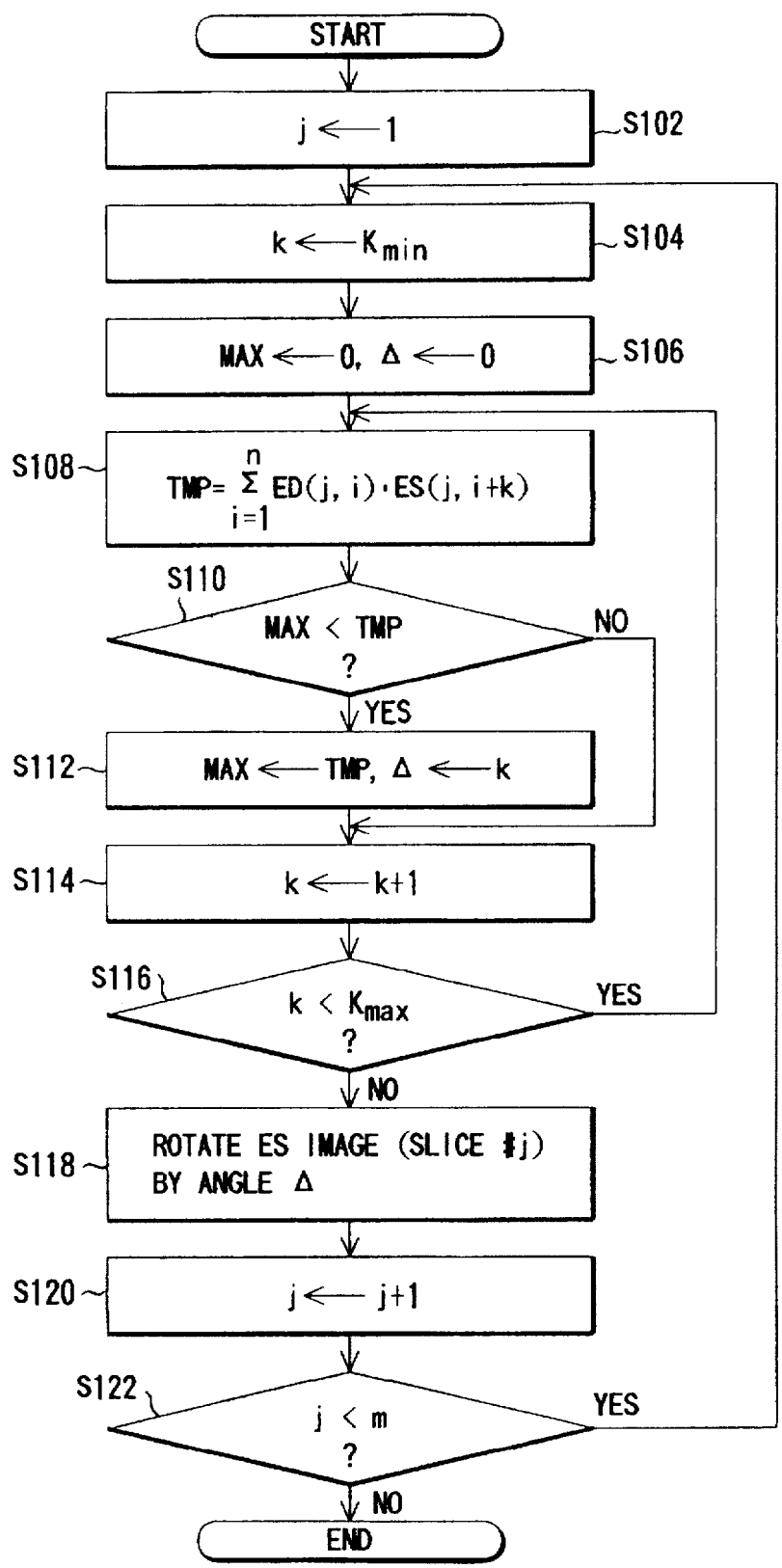
F I G. 6

IMAGE PROCESSING APPARATUS AND METHOD FOR QUANTITATIVELY DETECTING AND CORRECTING THE TWIST BETWEEN IMAGES

BACKGROUND OF THE INVENTION

1. Field of the Invention

The present invention relates to an image processing apparatus, and more particularly to a medicine image processing apparatus for correcting twist of the myocardium, adaptable to a nuclear medicine diagnosis apparatus, such as a single photon emission computed tomography (hereinafter called as a "SPECT") for scanning a tomograph image of the heart.

2. Description of the Related Art

In recent years, a SPECT apparatus has been employed to perform gated scan using a $^{99m}$Tc-labeled radiotracer for myocardium. The gated scan is an operation using R waves in an electrocardiogram as a trigger to detect gamma rays emitted from the radiotracer dosed into an object during a period in which the heart beats a predetermined number of times so as to acquire radiation-ray data. SPECT data indicating the short axis image of the heart is reconstructed from the acquired radiation-ray data. The image reconstruction is performed such that an image (hereinafter called an "ED image") of the myocardium at an end of diastole of the heart and an image (hereinafter called an "ES image") of the end of the systole of the heart are reconstructed. When the blood flow in the myocardium or the function of the heart is evaluated, SPECT data is developed on a polar coordinate plane to form a functional map.

An example of the functional map is shown in FIG. 1. FIG. 1 shows an example of the functional map of the left ventricle. The upper left portion of FIG. 1 shows an ED image, while the upper right portion shows an ES image. The lower portion of these images correspond to the apex of the heart, while the upper portions correspond to the base of the same. Slice numbers 1, 2, 3, 4 are sequentially given to slices starting from the apex. Assuming that the thickness of the slice is constant, the diameter of the long axis of the left ventricle is contracted due to the systole of the heart during shift from the ED image to the ES image, thus resulting in that the number of slices being decreased. Accordingly, the method shown in FIG. 1 is structured such that the respective slices of the ES image are overlapped on the adjacent slices to make the number of the slices of the ED image to be the same as the number of the ES images with maintaining the thickness of the slice constant.

A central point of the cavity of the heart is set, a plurality of straight lines are, in each slice, radially drawn from the central point, and the image of each slice is divided into a plurality of circumferential segments each having a predetermined angle. When SPECT data in each segment of all slices included in the ED image and the ES image is developed on the polar coordinate in such a manner that the radius is changed for each slice, a functional map or a radiation pattern image like a bull's-eye map can be obtained. That is, regions 1, 2, 3 and 4 in the functional map divided into the radial direction of the polar coordinate correspond to the slices, while regions divided in to the angular direction correspond to the segments obtained by dividing the slices as described above.

When the above-mentioned map is used, the blood flow in the myocardium or the like can be evaluated. As the parameter for evaluating the function of the heart, the thickness of the myocaridum wall (% wall thickening: % WT) expressed by the following equation is employed for example:

$$\% \text{ WT} = \frac{ES - ED}{ED} \times 100$$

where ES is a segment value in the ES image, ED is a segment value in the ED image, and % WT is calculated for each segment.

Therefore, the parameter for evaluating the function of the heart can be calculated only when the portions (the segments) of the ED image and those of the ES image are made to correspond to one another. However, the myocardium sometimes is twisted in a direction in parallel to the surface of the slice when contracted. That is, the direction of the reference segment is unintentionally shifted by an angular degree of $\theta$ in the functional map. Accordingly, a countermeasure has been made, in which the functional map of the ES image is rotated to correct the twist. The countermeasure is disclosed in "Assessement of Left Ventricular Function with $^{99m}$Tc-MIBI Gated Myocardial SPECT Using 3 Head Rotating Gamma Camera", pp. 43 to 52, No. 1, Vol. 31 of magazine "Department of Radiology, Nippon Medicine School", Sin-ichiro Kumita et al.

However, the method disclosed in the literature above is not arranged to quantitatively measure and detect the degree of twist but arranged such that an operator simply observes the functional map to sensuously correct the twist. Therefore, the twist cannot accurately be corrected since the degree of the twist does not uniformly take place over the heart and the myocardium sometimes is twisted in opposite directions between the apex of the heart and the base of the same when the heart is contracted. As a result, if the correction of the type in which the overall functional map (all slices) of the ES image is rotated in the same direction by the same angular degree involves a portion being corrected erroneously. Thus, the portions of the ED image and those of the ES image cannot be made to accurately correspond to one another. The above-mentioned method has a problem in that the parameter for evaluating the function of the heart cannot accurately be calculated.

SUMMARY OF THE INVENTION

Accordingly, it is an object of the present invention to provide an image processing apparatus which quantitatively detects the twist between at least two images so as to accurately correct the twist.

A related object of the present invention is to provide an image diagnosis apparatus for performing gated scan to make a functional map from SPECT data so as to evaluate the function of the heart, which prevents shift of the functional map at the end of diastole of the heart and that at the end of systole of the same in the direction of rotation even if the myocardium is twisted when the heart is contracted.

A further object of the present invention is to provide an image diagnosis apparatus for performing gated scan to make a functional map from obtained SPECT data so as to evaluate the function of the heart, which prevents shift of the functional map at the end of diastole of the heart and that at the end of systole of the same in the direction of rotation by correcting the twist for each slice even if the myocardium is twisted in opposite directions between the apex of the heart and the base of the same when the heart is contracted.

A still further object of the present invention is to provide an image diagnosis apparatus for comparing two images with each other to diagnose the image, which automatically corrects twist between the two images to accurately make the rotation-directional positions to correspond to each other.

According to the present invention, there is provided an image processing apparatus for correcting twist between two images, comprising means for dividing each image into angular segments relative to a predetermined point; and processing means which compares image data in a certain segment of one image serving as a reference and image data in a predetermined number of segments of another image to one another to determine a segment of the other image having a minimum difference and detect a degree of twist.

According to the present invention, there is provided a nuclear medicine diagnosis apparatus comprising reconstruction means for detecting radiation rays emitted from an object in synchronization with an electrocardiogram of the object so as to reconstruct a first tomograph image of a myocardium at an end of diastole and a second tomograph image of the myocardium at an end of systole; means for developing the first and second tomograph images on a polar coordinate so as to make first and second radiation pattern images; means for detecting an amount of shift in a rotational direction of the first and second radiation pattern images of predetermined slices in the radiation pattern image; and twist correction means for rotating at least either of the first and second radiation pattern images in accordance with the detected amount of the shift.

According to the present invention, there is provided a method of correcting twist of images, comprising the following steps of dividing an image into a plurality of angular segments relative to a certain point; comparing distribution patterns of segment data of two images to detect the amount of shift between the two images in the direction of the segments; and correcting the twist by rotating at least either image by a detected amount of shift.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 3 is a flow chart showing the overall operation of the embodiment;

FIG. 6 is a flow chart showing a detailed process for correcting twist.

DETAILED DESCRIPTION OF THE PREFERRED EMBODIMENTS

Figure 1:
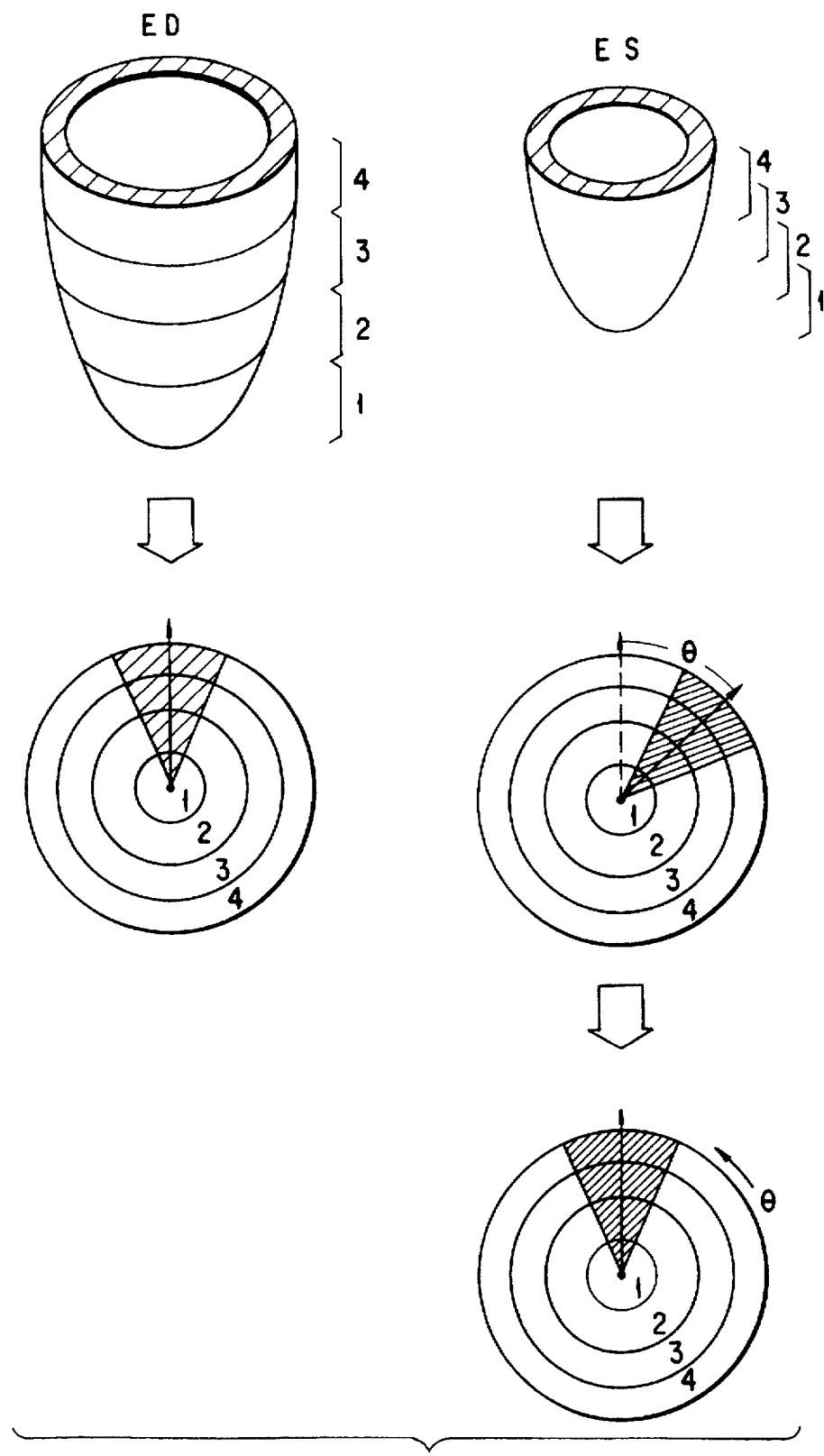
FIG. 1 is a diagram showing a functional map made from SPECT data without twist correction.
Figure 2:
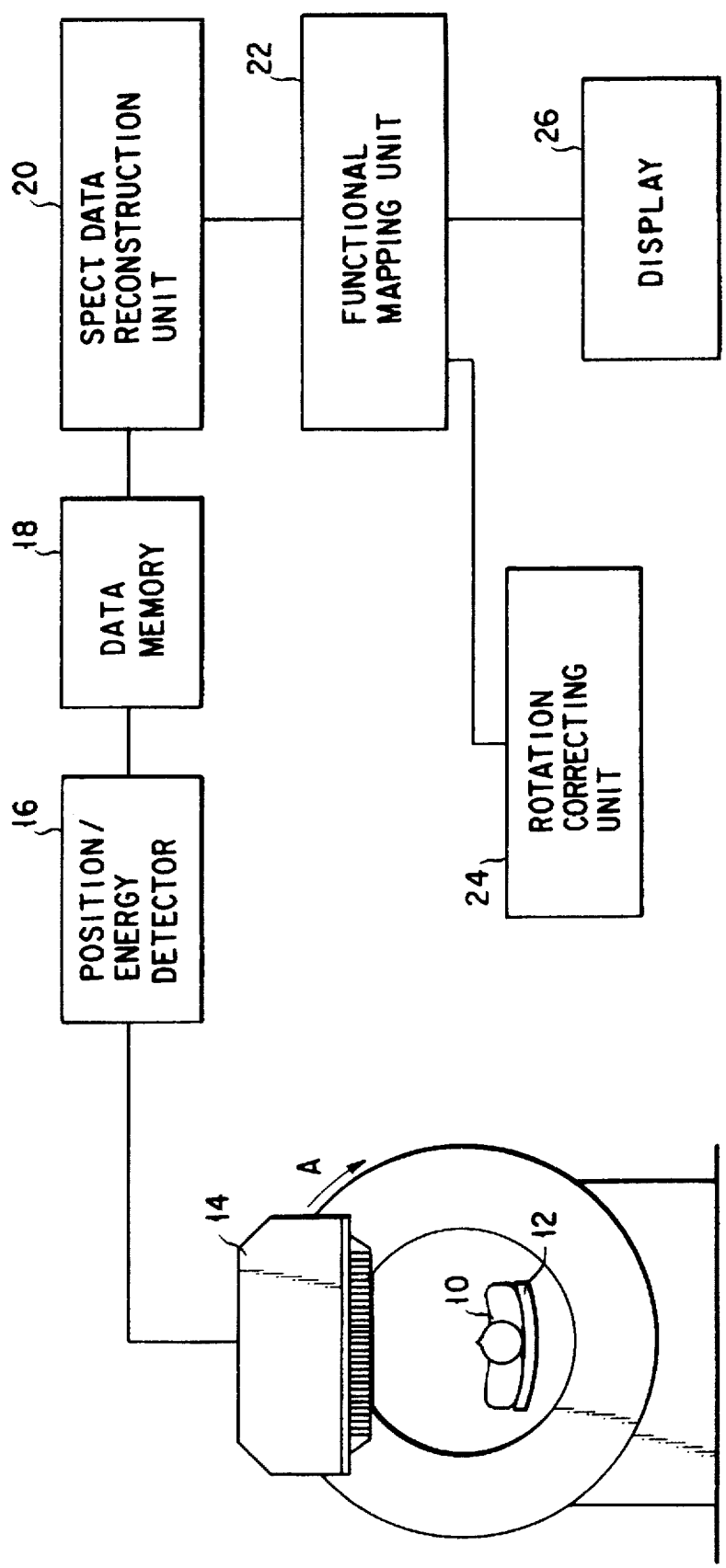
FIG. 2 is a block diagram of a SPECT apparatus according to an embodiment of the present invention.

A preferred embodiment of an image processing apparatus according to the present invention will now be described with reference to the accompanying drawings. The embodiment of the image processing apparatus is adapted to a SPECT apparatus. FIG. 2 is a block diagram showing the schematic structure of the SPECT apparatus. A detector 14 is disposed rotatively around a bed 12 on which an object 10 is placed, the detector 14 being rotative in a direction indicated by an arrow A. Although FIG. 2 shows a detection surface of the detector 14 which is in parallel to the bed 12, the detection surface can be inclined arbitrarily so that a tomograph image in an arbitrary direction is scanned. Since a mechanism for supporting/rotating the detector 14 has a similar structure to that of the X-ray CT apparatus, detailed description of the supporting/rotating mechanism is omitted here.

The detector 14 has a scintillator formed into a plate-like shape to absorb energy of gamma rays emitted from RI(radio isotope) or radiotracer dosed into the body of the object so as to generate fluorescent light at the point upon which the gamma rays are made incident; and a collimator disposed on the incident surface of the scintillator and having a multiplicity of parallel apertures (incident apertures), the collimator being made of a lead plate. A plurality of photomultipliers are provided on the backside of the scintillator through a light guide. Therefore, when gamma rays are made incident upon the detector 14, the incident points of the scintillator emit light beams. The light beams are allowed to pass through the light guide, and then made incident upon the plural photomultipliers so as to be photoelectrically converted. Therefore, whenever the gamma rays are made incident upon the photomultipliers, the photomultipliers outputs pulse signals, the level of each of which is in proportion to the intensity of the incident light.

This pulse signal is supplied to a position/energy detector 16. The position/energy detector 16 has a pre-amplifier, a weighting resistor, and an adder to calculate the position and energy of the incident gamma ray in accordance with the pulse signal supplied from the photomultiplier whenever the gamma ray is made incident upon the photomultiplier. Moreover, the position/energy detector 16 corrects the linearity of the obtained position and energy so as to transmit a digital energy signal and a digital position signal each corresponding to results of the calculations.

The above-mentioned signals are temporarily stored in a data memory 18, and then supplied to a SPECT data reconstruction circuit 20 so that SPECT data showing the tomograph image is reconstructed. The SPECT data is supplied to a functional mapping circuit 22 so that a functional map of the ED image and that of the ES image are generated. A rotation correcting circuit 24, which is the characteristic feature of the present invention, is connected to the mapping circuit 22 so that deviation in the rotation of the functional map of the ES image occurring due to twist of the myocardium is compensated. A corrected functional map is displayed by a display portion 26.

The operation of this embodiment will now be described. In step S10, a radiotracer is dosed to an object, as shown in FIG. 3. In step S12, radiation rays emitted from the radiotracer are detected while the detector 14 is rotated. Since the detector 14 has a large field of view, data of a plurality of slices is obtained in a single rotation of the detector 14. As the radiotracer, Tc or the like is used, which has a short half time and can be dosed in a large quantity. The radiation rays are, during several heart beats, detected at the end of diastole of the myocardium and at the end of systole of the same by using, as a trigger, an R wave in an electrocardiogram obtained from an electrocardiograph (not shown) attached to the object. For example, the radiation rays are detected during 70 heart beats and an interval R—R is equally divided into sixteen sections.

In step S14, a SPECT short axis image (the ED image) at the end of diastole and a SPECT short axis image (the ES image) at the end of systole each comprised of a predetermined number of slices are reconstructed from the detected radiation-ray data.

Figure 4:
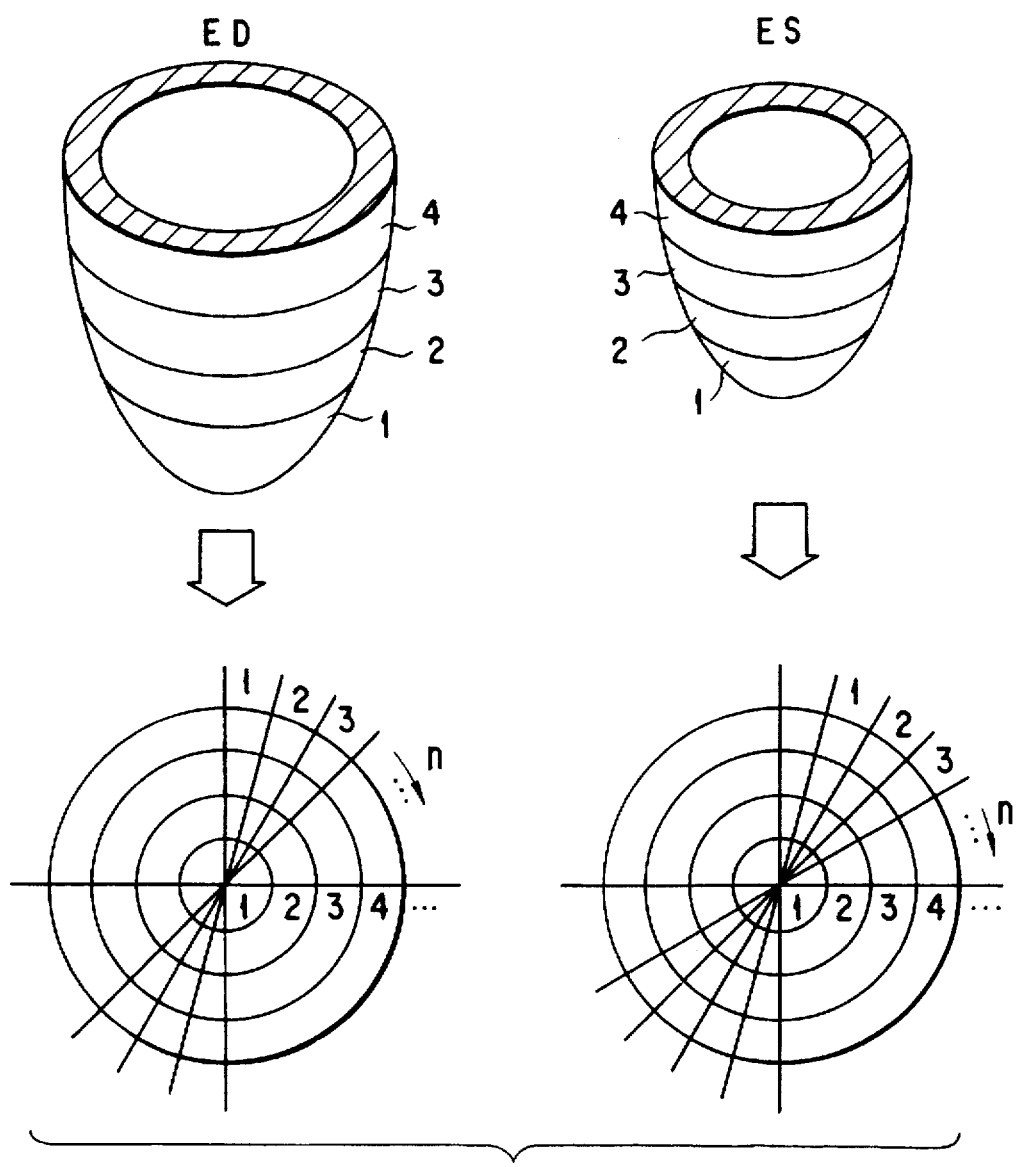
FIG. 4 is a diagram showing the functional map according to the embodiment.

In step S16, all slices of the reconstructed SPECT short axis image at the ends of the diastole and systole are divided into angular segments. Then, the segment values are developed on the polar coordinate so that a functional map or a radiation pattern image shown in FIG. 4 is formed.

In this embodiment, the functional map is formed such that the polar coordinate plane is divided into m sections in the radial direction and into n sections in the angular direction. Moreover, the (radius of) ES image is normalized with reference to the ED image. One section obtained by the division in the radial direction corresponds to a slice. Moreover, sections are arranged such that inner portions show the segment values of the apex of the heart and the outer portions show the base of the heart. One section obtained by the division in the angular direction is called a segment, and the segments are given sequential segment numbers.

To quantitatively determine a state of blood flow in the myocardium in accordance with the functional map, % WT is calculated for example. However, since the myocardium sometimes is, as described above, twisted when contracted, corresponding segments of the ED image and the ES image are, by plural segments, shifted one another in the angular direction. Therefore, the evaluation of the function of the heart cannot be performed by simply comparing the two images. Accordingly, this embodiment performs a compensation procedure in step S18 in which twist of the myocardium is corrected. Then, the diagnosis is performed in step S20.

The method of correcting twist will now be described with reference to FIGS. 5A, 5B, and 6. The segment value of segment number i of slice j of the ED image is made to be ED (j, i) and the segment value of the segment number i of slice j of the normalized ES image is made to be ES (j, i). Note that the segment value may be the maximum value or a mean value of SPECT data in the target segment which is permitted to be selected by an operator.

Figure 5A:
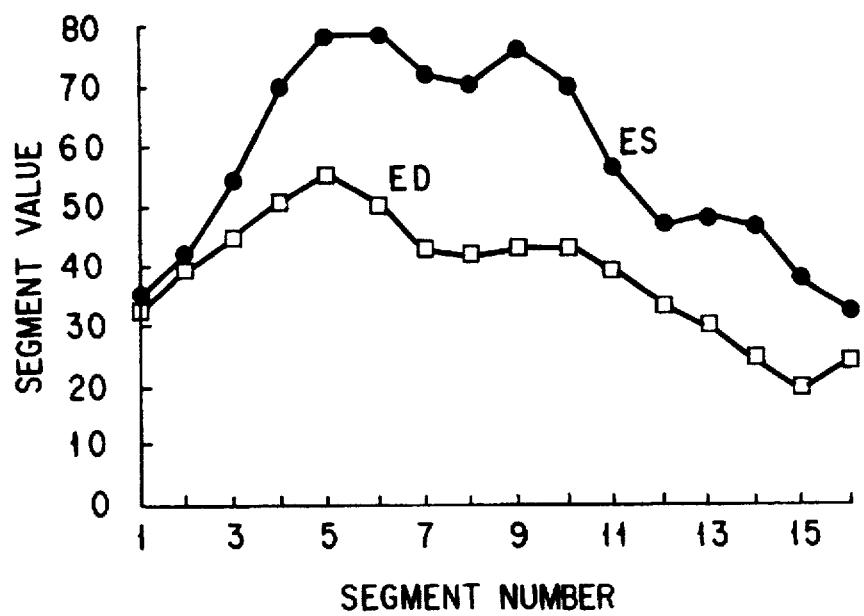
FIGS. 5A and 5B are graphs showing a pattern of segment values for explaining the principle of correction of twist.
Figure 5B:
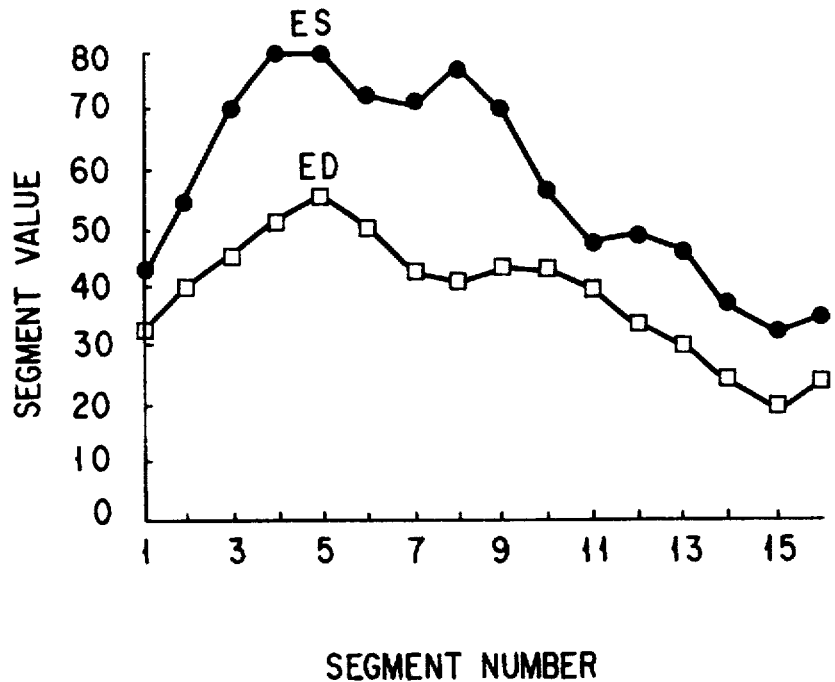

FIGS. 5A and 5B show a graph of plotting of certain slices of the ED image and the normalized ES image such that the axis of abscissa stands for the segment numbers and the axis of ordinate stands for the segment values. FIG. 5A shows the value before correction and FIG. 5B shows the corrected value. The larger segment value indicates large blood flow, while a myocardial infraction portion or the like has a small segment value. The above-mentioned relationship applies commonly regardless whether the timing is the end of the diastole and that of systole. The end of diastole of the myocardium and the end of systole of the same are different from each other in the segment value of the quantity of blood flow or the like in the corresponding portions. In the case shown in FIG. 5A, the overall pattern, including the peak positions (segment numbers), of the ES image is shifted in the right-hand direction from the ED image by about one segment. As described above, the shift of the segment value pattern of the ES image shown in FIG. 5A indicates occurrence of twist of the myocardium. By detecting the amount of the shift and by rotating the functional map of the ES image by a degree corresponding to the detected shift amount, shift in the functional map of the ES image and the ED image occurring due to the twist of the myocardium can be eliminated.

A flow chart of a method of correcting twist of the myocardium is shown in FIG. 6. The correction of the twist of the myocardium is performed independently for each slice j. Initially, in step S102, "1" is set to variable j indicating the slice. In a bull's-eye map, j=1 in the central circular region.

In step S104, minimum value Kmin is set to variable k indicating a segment in the angular direction from which the twist is detected. Although detection of twist may be performed in all segments, it is wasteful to process all segments in terms of time saving because twist can be detected in only portions. Since the portions in which twist is occurred have been recognized due to experiments, the portions are, with the segment numbers, previously instructed by the operator. In this case, Kmin to Kmax are instructed. For example, Kmin is made to be −4 and Kmax is made to be +4.

In step S106, "0" is set to variables MAX and Δ which are used in a calculation to be performed later.

In step S108, a sum of products (pattern matching) of the segment value of the ED image and the segment value of the ES image are obtained as follows:

$$TMP = \sum_{i=1}^{n} ED(j,i) \times ES(j, i+k)$$

A case where the sum of products is the largest value can be determined to be the original position of the ES image in the rotational direction without twist of the myocardium with respect to the ED image.

Therefore, the region of slice j of the ES image is rotated counterclockwise by an angular degree corresponding to the value (which is set to variable Δ as described later) of variable k in the segment direction so that twist of slice j of the ES image is corrected. Since the maximum value of the variable i in the segment direction is n, n is subtracted as follows if i+k is larger than n:

$$ED (j, i+n)=ED (j, i)$$

$$ES (j, i-n)=ES (j, i)$$

To detect the maximum value of TMP, variable TMP is compared with variable MAX in step S110. If variable TMP is larger than variable MAX, variable MAX is updated with variable TMP, and then k is set to variable Δ in step S112. In step S114, k is increased by one. If variable TMP is not larger than variable MAX, the operation directly proceeds to step S114.

In step S114, k is updated so that k is increased by one. In step S116, whether k is not more than Kmax is determined. If k is not more than Kmax, the sum of products has not been obtained for all segments, which are the subjects from which the twist of the ES image is detected. Therefore, the operation returns to step S108.

If k is more than Kmax, the sum of products has been obtained for all segments. Therefore, the region of slice j of the ES image is, in step S118, counterclockwise rotated by the obtained angle Δ so that twist is corrected. Although angle Δ is obtained as the clockwise angle, the angle of rotation for the correction is made to be the counterclockwise direction. Note that the rotational direction is not limited to this.

To subject all slices to the above-mentioned process, slice variable j is increased by one in step S120. In step S122, whether j is not more than m (m: the maximum slice number) is determined. If j is m or less, the operation returns to step S104 so that a process for a next slice is repeated. If j is not m or less, all slices have been subjected to the process. Thus, the twist correction process for all the slices is completed here.

As described above, according to this embodiment, pattern matching of the ED image and the ES image is performed for each of the regions corresponding to the slices of the functional maps so that the degree of twist is detected and rotation is performed for each slice region so as to correct the twist. Therefore, twist between two medicine diagnosis images is quantitatively determined so that correction is accurately performed. Even if the myocardium is twisted in the opposite directions between the apex and the base when the heart is contracted, twist can accurately be corrected. As a result, the segment regions in the functional map of the ED image and the functional map of the ES image can be made to accurately correspond to one another. The parameter, for example, % WT, for evaluating the function of the heart can accurately be obtained.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, the foregoing embodiment having the structure such that twist of the myocardium is detected and corrected for all slices may be modified such that the degree of twist of the myocardium is detected at every several slices because the degree of twist is substantially the same over the several adjacent slices. As for the several slices, the degree of twist may be obtained by interpolating the detected values for the two slices.

Although the above-mentioned embodiment has the structure such that the degree of twist is calculated from the segment value in the functional map made by developing SPECT data on the polar coordinate, the functional map is not needed to be made. That is, the degree of twist may be obtained directly from SPECT data.

In the above-mentioned embodiment, the amount of correction is obtained by performing a matching using the maximum value of the sum of products of the SPECT data of the segments obtained by, in the radial direction and the angular direction, dividing the short axis images (the ED image and the ES image) obtained by the SPECT apparatus. However, a value for each segment calculated from image data obtained by another nuclear medicine processing apparatus or a value for each segment of tagging information collected by an MRI apparatus may be used to perform similar operation.

Although the description has been performed about the short axis image of the heart, the present invention is not limited to the medicine image.

As described above, according to the present invention, there is provided an image processing apparatus capable of quantitatively detecting at least two images and accurately correcting the twist. Moreover, an image diagnosis apparatus, which performs gated scan to make a functional map from SPECT data so as to evaluate the function of the heart prevents twist of the functional maps for the end of diastole and the end of systole in the rotational direction even if the myocardium is twisted when the heart is contracted. Moreover, even if the myocardium is twisted in opposite directions between the apex and the base of the heart, an image diagnosis apparatus of the foregoing type prevents twist of the functional map for the end of diastole and that for the end of systole by performing correction for each slice. Therefore, an image diagnosis apparatus, which compares two images, is enabled to automatically correct twist between two images so as to make the rotational positions to correspond to each other.

What is claimed is:

1. An image processing apparatus comprising:
   reconstruction means for detecting radiation rays emitted from an object in synchronization with an electrocardiogram of the object so as to reconstruct a first image of a myocardium at an end of diastole and a second image of the myocardium at an end of systole, the first and second images having first and second tomographic images of plural slices;
   means for developing the first and second tomographic images on a polar coordinate system;
   means for detecting an amount of shift in a rotational direction between the first and second tomograph images of each slice; and
   twist correction means for rotating at least either of the first and second tomographic images of each slice in accordance with the detected amount of the shift.

2. An apparatus according to claim 1, in which said first and second tomographic images are perpendicular to an axial line connecting an apex of a heart of the object and a base of the heart.

3. An apparatus according to claim 1, in which the first and second tomographic images of each slice are divided into plural segments in a circumferential direction, and said detecting means comprises means for detecting the amount of shift of a segment with which a difference between segments is made to be minimum.

4. An apparatus according to claim 3, in which said detecting means detects an amount of shift of the segment with which a sum of products of values of segments of the first and second tomographic images is made to be maximum.

5. An apparatus according to claim 4, in which said detection means obtains a value k with which a following calculation is made to be maximum:

$$\sum_{i=n1}^{n2} ED(j,i) \times ES(j,i+k)$$

where i is the segment number, j is the slice number, ED (j,i) is the value of the segment i in the slice j of the first radiation pattern image, ES (j,i) is the value of the segment i in the slice j of the second radiation pattern image, n1 and n2 are arbitrarily integers, and k is a variable for changing the segment, the sum of products of which is obtained.

6. An apparatus according to claim 5, in which said developing means develops the first tomographic image on the same plane with changing the radial directional positions of the first tomographic image of the plural slices to form a first bull's-eye map and develops the second tomographic images on the same plane with changing the radial directional positions of the second tomographic images of the plural slices to form a second bull's-eye map;
   said detecting means calculates the amount of shift of all slices; and
   said twist correction means corrects all the slices using the amount of shift calculated of all the slices.

7. An apparatus according to claim 5, in which said developing means develops the first tomographic image on the same plane with changing the radial directional positions of the first tomographic image of the plural slices to form a first bull's-eye map and develops the second tomographic images on the same plane with changing the radial directional positions of the second tomographic images of the plural slices to form a second bull's-eye map;

said detecting means calculates the amount of shift of only predetermined slices and interpolates the amount of shift of the other slices; and said twist correction means corrects all the slices using the amount of shift calculated of all the slices.

8. An image processing apparatus for correcting twist of myocardium which is divided into plural slices in a radial direction, each slice being divided into plural segments in a circumferential direction, comprising:

means for comparing segment data for each slice of a given myocardium and corresponding segment data of reference myocardium to detect a degree of twist for each slice; and means for rotating each slice of the given myocardium based on the degree of twist detected by said comparing means.

9. An image processing apparatus according to claim 8, in which said comparing means obtains a value k with which a following calculation is made to be maximum:

$$\sum_{i=n1}^{n2} ED(j,i) \times ES(j,i+k)$$

where i is the segment number, j is the slice number, ED (j,i) is the value of the segment i in the slice j of the first radiation pattern image, ES (j,i) is the value of the segment i in the slice j of the second radiation pattern image, n1 and n2 are arbitrary integers, and k is a variable for changing the segment, the sum of products of which is obtained.

10. A method for correcting a myocardium twist, comprising the steps of:

dividing the myocardium into plural slices in a radial direction, and dividing respective of said plural slices into plural segments in a circumferential direction;

comparing segment data for each slice of the myocardium with corresponding segment data of a reference myocardium;

detecting a degree of twist for each slice based on the comparison result obtained in said comparison step; and rotating each slice of the myocardium based on degree of twist detected in said detecting step.

11. The method of claim 10 wherein:

said comparing step includes obtaining a value k with which the following calculation is made to be maximum, $$\sum_{i=n1}^{n2} ED(j,i) \times ES(j,i+k)$$

where i is the segment number, j is the slice number, ED (j,i) is the value of the segment i in the slice j of the first radiation pattern image, ES (j,i) is the value of the segment i in the slice j of the second radiation pattern image, n1 and n2 are arbitrary integers, and k is a variable for changing the segment, the sum of products of which is obtained.

12. An image processing method, comprising the steps of:

detecting radiation rays emitted from an object in synchronization with an electrocardiogram of the object so as to reconstruct a first image of a myocardium at an end of a diastole and a second image of the myocardium at an end of systole, including, reconstructing the first image to have a first tomographic image of plural slices, and reconstructing the second image to have second tomographic images of plural slices;

developing the first and second tomographic images on a polar coordinate;

detecting an amount of shift in a rotational direction between the first and second tomographic images of each slice; and rotating at least one of the first and second tomographic images of each slice in accordance with the detected amount of the shift.

13. The method of claim 12, wherein the reconstructing steps respectively include reconstructing the first tomographic images and the second tomographic images to be perpendicular to an axial line connecting an apex of a heart of the object and a base of the heart.

14. The method of claim 12, wherein:

the reconstructing steps respectively include reconstructing the first tomographic images and the second tomographic images of each slice by dividing the respective slices into plural segments in a circumferential direction; and said detecting step, comprises detecting the amount of shift of a segment with which a difference between segments is made to be minimum.

15. The method of claim 14, wherein said step of detecting the amount of shift, comprises detecting the amount of shift of the segment with which a sum of products of values of segments of the first tomographic images and the second tomographic images is made to be maximum.

16. The method of claim 15, wherein said step of detecting includes obtaining a value k with which the following calculation is to be made maximum, $$\sum_{i=n1}^{n2} ED(j,i) \times ES(j,i+k)$$

where i is the segment number, j is the slice number, ED (j,i) is the value of the segment i in the slice j of the first radiation pattern image, ES (j,i) is the value of the segment i in the slice j of the second radiation pattern image, n1 and n2 are arbitrarily integers, and k is a variable for changing the segment, the sum of products of which is obtained.

17. The method of claim 16 wherein: said developing step comprises developing the first tomographic image on the same plane with changing the radial directional positions of the first tomographic image of the plural slices to form a first bull's-eye map and developing the second tomographic images on the same plane with changing the radial directional positions of the second tomographic images of the plural slices to form a second bull's-eye map;

said step of detecting the shift amount, including calculating the amount of shift slices; and correcting all the slices using the amount of shift of all slices calculated in said calculating step.

18. The method of claim 16, wherein: said developing step comprises developing the first tomographic image on the same plane with changing the radial directional positions of the first tomographic image of the plural slices to form a first bull's-eye map and developing the second tomographic images on the same plane with changing the radial directional positions of the second tomographic images of the plural slices to form a second bull's-eye map;

said step of detecting the amount of shift, includes calculating the amount of shift of only predetermined slices and interpolating the amount of shift of the other slices; and correcting all of the slices using the amount of shift of all slices calculated in said calculating step.

* * * * *